(12) United States Patent
Jonson

(10) Patent No.: US 6,709,405 B2
(45) Date of Patent: Mar. 23, 2004

(54) BREATHING APPARATUS AND METHOD FOR OPERATION THEREOF FOR EXAMINING PULMONARY MECHANICS OF A RESPIRATORY SYSTEM

(75) Inventor: Björn Jonson, Lund (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 10/245,898

(22) Filed: Sep. 17, 2002

(65) Prior Publication Data

US 2003/0078512 A1 Apr. 24, 2003

(30) Foreign Application Priority Data

Sep. 25, 2001 (SE) ................................. 0103182

(51) Int. Cl.[7] ......................... A61B 5/08; A61M 16/00; A62B 7/00; A62B 7/04; F16K 81/26
(52) U.S. Cl. ................. 600/538; 600/529; 128/204.21; 128/204.22; 128/204.26
(58) Field of Search ................... 600/538, 529, 600/531, 532, 533, 537; 128/200.24, 204.18, 204.21, 204.23, 204.26

(56) References Cited

U.S. PATENT DOCUMENTS

| | | | |
|---|---|---|---|
| 3,741,208 A | * | 6/1973 | Jonsson et al. ........ 128/204.21 |
| 4,844,085 A | | 7/1989 | Gattinoni |
| 5,429,123 A | * | 7/1995 | Shaffer et al. ......... 128/204.23 |
| 5,575,283 A | * | 11/1996 | Sjoestrand ............ 128/204.23 |
| 5,884,622 A | | 3/1999 | Younes |
| 5,937,854 A | | 8/1999 | Stenzler |
| 6,142,952 A | | 11/2000 | Behbehani et al. |

FOREIGN PATENT DOCUMENTS

| | | |
|---|---|---|
| SE | 50 6521 | 10/1995 |
| WO | WO 01/68162 | 9/2001 |

OTHER PUBLICATIONS

"Analog Circuit For Real–Time Computation Of Respiratory Mechanical Impedance In Sleep Studies," Farré et al, IEEE Tans. On Biomedical Engineering, vol. 44, No. 11, Nov. 1997, pp. 1156–1159.

* cited by examiner

Primary Examiner—Max F. Hindenburg
Assistant Examiner—Navin Natnithithadha
(74) Attorney, Agent, or Firm—Schiff Hardin LLP

(57) ABSTRACT

In an apparatus and method for examining the pulmonary mechanics of a respiratory system, in order to obtain information about the mechanical properties of the respiratory system's lungs, during an expiration of a flow of gas streaming out of the respiratory system is modulated, the volume of gas streaming out of the respiratory system is determined, the variation in pressure in the respiratory system is determined, and an expiratory pressure-volume relationship is determined from the expiratory volume and the expiratory variation in pressure.

17 Claims, 3 Drawing Sheets

BREATHING APPARATUS AND METHOD FOR OPERATION THEREOF FOR EXAMINING PULMONARY MECHANICS OF A RESPIRATORY SYSTEM

BACKGROUND OF THE INVENTION

1. Field of the Invention

The present invention relates to a method for examining the pulmonary mechanics of a respiratory system.

The present invention also relates to a breathing apparatus system operating according to the method.

2. Description of the Prior Art

A ventilator is an apparatus for ventilating or supporting spontaneous ventilation of the lungs of a human being or an animal, hereafter referred to as the 'patient'. The procedure generally employed for tailoring a ventilator's operation to physiological conditions prevailing in the patient is for the responsible care-provider to obtain as much information as possible about the patient, information about the respiratory organs in particular. This type of information often can be obtained when the ventilator is equipped with sensors for airway pressure, flow or volume delivered to or removed from the respiratory organs. Measurement systems, however, often are formed of one or a number of devices independent of the ventilator. The measurement systems can be linked to systems for analysing pulmonary function. Thus, measurement signals for pressure, volume and flow can be deployed so as to yield information about the elasticity of the respiratory organs, referred to below as compliance, or about resistance to flow in the airways. Ventilators can contain and/or be connected to computers that read the signals from sensors and analyse them. Computers or electronic circuits incorporated in the respirator, hereafter referred to as 'the computer', act on the ventilator's functional modes and cause the ventilator to perform test breaths yielding increased information about pulmonary function. Test breaths of this kind can mean that the computer controls both inspiration and expiration for obtaining the desired physiological information.

One example of such control is disclosed in Swedish Patent No. 506521, which describes control whereby expiration is affected in such a way that its duration is prolonged, and a constant target airway pressure is maintained. This expiration is followed by an inspiration during which the flow is modulated, e.g. with a sinusoidal waveform. The variation in flow during inspiration leads to corresponding variations in airway pressure. The relationship between variations in pressure and flow reflects resistance in the respiratory system. This resistance can be calculated. At the same time, the respiratory system's elastic rebound pressure can be calculated in relation to the insufflated volume. This yields the respiratory system's elastic pressure/volume curve, i.e. the $Pel_I/V$ curve. The $Pel_I/V$ curve is believed to supply information about the positive end-expiratory pressure (PEEP) required to keep open the lungs of a patient with acute respiratory distress syndrome (ARDS). This has been questioned, however, since the morphology of the $Pel_I/V$ curve is influenced by complex phenomena and therefore difficult to interpret. Multiple $Pel_I/V$ curves recorded at different levels of PEEP can supply more detailed information, but recording these curves is difficult and time-consuming.

For some time, it has been known that the recording of both inspiratory and expiratory pressure-volume curves, thereby yielding a pressure-volume loop, supplies information about the forces required to open a collapsed lung. A significant difference between the inspiratory curve and the expiratory curve gives the loop a large area referred to as large hysteresis. The greater the hysteresis, the greater the tendency of the lung to collapse and resist re-expansion, so-called recruitment. This means that internal forces in the lung are particularly strong during recruitment, and this poses a great risk of respirator-induced lung damage (RILS).

Elastic pressure-volume curves for inspiration and expiration, together with the Pel/V loops, were previously recorded during respirator treatment using a 'jumbo' syringe. This is disclosed in e.g. U.S. Pat. No. 4,844,085. Recording takes a long time. This means that gas exchange in the form of gas uptake leads to artifacts, making accurate determination of hysteresis impossible.

Pel/V loops also can be determined with the flow occlusion method. This determination takes several minutes during which the patient's condition can change, thereby making accurate determination of hysteresis impossible in clinical settings. No methods are available for accurate, automatic measurement of pressure-volume loops in clinical practice.

SUMMARY OF THE INVENTION

An object of the present invention is to provide a method for examining pulmonary mechanics that solves at least some of the aforementioned problems of the known methods.

Another object of the present invention is to provide a respiratory apparatus system for use in the examination of pulmonary mechanics and in the treatment of respiratory systems (in humans and animals). The system must be easy to use in examinations of pulmonary mechanics in clinical settings without affecting ongoing treatment of the respiratory system.

Another object of the present invention is to provide a breathing apparatus system, and a method for the operation thereof, for automatic regulation of respiratory parameters on the basis of the respiratory system's mechanical condition.

The above object is achieved in accordance with the principles of the present invention in a method for operating a breathing apparatus for examining the pulmonary mechanics of a respiratory system communicating with the breathing apparatus, wherein the flow of gas exiting from the respiratory system is modulated, the volume of the gas exiting the respiratory system is determined, the variation in pressure in the respiratory system is determined, and an expiratory pressure-volume relationship is determined from the aforementioned volume and the aforementioned pressure.

The elastic properties of the respiratory system can be established in a simpler fashion during expiration by modulating the flow of gas streaming out of the respiratory system. Volume and pressure are determined in relation to time during expiration and can then be used for determining an expiratory pressure-volume relationship. The relationship obtained refers advantageously to the elastic part of the ratio, i.e. the resistive components have been subtracted.

Modulation can be sinusoidal, triangular, quadratic or have some other regular shape. Declining or increasing modulation with a regular basic form or even completely irregular modulation can be used. Pressure can be measured inside the respiratory system, e.g. in the airways, or at some other location in the path of gas from the respiratory system. When pressure is not measured in the respiratory system itself, the corresponding pressure can be calculated from the measured pressure by compensating for the pressure drop in the system of tubing etc. Measuring the flow and integrating it determine the volume most easily. However, other ways of determining volume are possible.

The expiratory pressure-volume relationship (which can be represented by a curve in a system of co-ordinates) can be determined in the corresponding manner by modulating flow during inspiration. Comparison supplies a measure of hysteresis. Hysteresis can then be used for evaluations in the known manner.

Repeating the method for a number of breaths would be advantageous. A number of normal breaths should then be allowed between these test breaths. This is especially the case when the pressure-volume relationship for inspiration is established after a preceding expiration with a prolonged duration.

The above object also is achieved in accordance with the present invention in a breathing apparatus for use in examination and treatment of the pulmonary mechanics of a respiratory system, having a pneumatic unit for regulating the flow and pressure of gases, a measurement sensor system for measuring pressure and flow, a control unit connected to the pneumatic unit for control thereof and to the measurement sensor system to receive measurement signals therefrom, and a tubing system connected to the pneumatic unit and connectible to the respiratory system, wherein the control unit controls the pneumatic unit during expiration so that the pneumatic unit modulates a flow of gas exiting from the respiratory system, and wherein the control unit determines an expiratory pressure-volume relationship from measurement signals from the measurement sensor system.

In principle, the control unit in the breathing apparatus system is devised to permit control of test breaths according to the described method.

The control unit also can be devised to perform automatic changes in certain parameters on the basis of results obtained for hysteresis. PEEP, tidal volume and frequency in particular can be parameters for automatic control.

DESCRIPTION OF THE PREFERRED EMBODIMENTS

Figure 1:
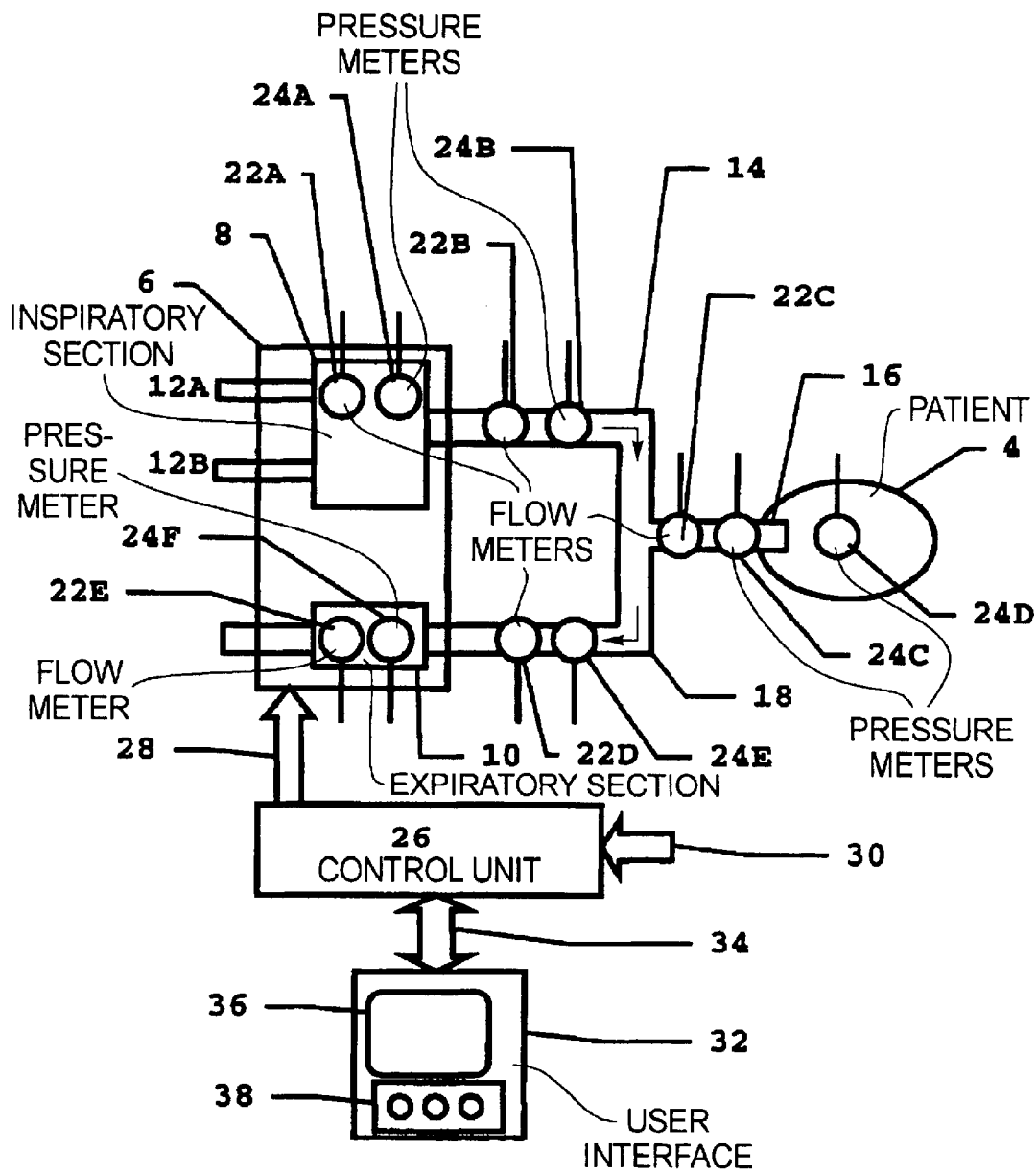
FIG. 1 is a schematic overview of a breathing apparatus system according to the invention.

FIG. 1 shows a breathing apparatus system 2 connected to a patient 4. The system is only schematically depicted, since the configuration options available with modern technology are virtually unlimited.

The system 2 has a pneumatic unit 6. The pneumatic unit 6 contains the components necessary for regulating the flow and pressure of a breathing gas delivered to or removed from the patient 4. Thus, the pneumatic unit 6 has an inspiratory section 8 and an expiratory section 10. The inspiratory section 8 can include valves for regulating a number of pressurized gases connected by gas connectors 12A, 12B. Alternatively, the inspiratory section can include a pressure/flow-generating component such as a compressor, pump, fan etc. The expiratory section 10 can include a valve.

The system 2 also has a system of tubing for carrying gas to and from the patient 4. The system of tubing usually includes an inspiratory tube 14, a patient connector 16 (e.g. a facemask or a tracheal tube) and an expiratory tube 18.

A system of measurement sensors is employed for measuring the flow and pressure of breathing gas. The system can include one or a number of flow meters 22A and 22B and one or a number of pressure meters 24A and 24B. For example, one flow meter 22A can be arranged in the inspiratory section 8, one flow meter 22B in the inspiratory tube 14, one flow meter 22C in the patient connector 16, one flow meter 22D in the expiratory tube 18 and one flow meter 22E in the expiratory section 10. Only one of the first three flow meters 22A through 22C is necessary for determining inspiratory flows and volumes, and only one of the last flow meters 22C or 22E is necessary for determining expiratory flows and volumes. Thus, a single flow meter 22C in the patient connector 16 can be used for determining both inspiratory and expiratory flows.

In a corresponding manner, one pressure meter 24A can be arranged in the inspiratory section 8, one pressure meter 24B in the inspiratory tube 14, one pressure meter 24C in the patient connector 16, one pressure meter 24D in the patient 4, one pressure meter 24E in the expiratory tube 18 and one pressure meter 24F in the expiratory section 10. In principle, a single pressure meter (any of 24A through 24F) can be used for determining the pressure in all parts of the system 2 and the respiratory system of the patient 4. Compensation for the drop in pressure caused by resistances etc. would then be necessary.

A control unit 26 controls the pneumatic unit 6 by transmission (wired or wireless) of a signal 28. The control unit 26 can receive measurement signals from the measurement sensor system via a signal input 30 (wired or wireless). The control unit 26 contains hardware and software for performing the functions it is to control and monitor. The control unit 26 also contains the hardware and software required for performing calculations according to the method taught in the invention.

The control unit 26 is able to communicate with a user interface 32 by transmission (wired or wireless) of a signal 24. The user interface 32 suitably comprises a screen or display 36 and an input section 38. The display 36 also can contain input facilities employing touch controls.

All the stipulated parts can be integrated into a single apparatus or functionally distributed among different apparatuses. Thus, the latter option could mean that e.g. the inspiratory section 8 and part of the control functions in the control unit 26 are physically located in one apparatus (e.g. the ventilator), whereas e.g. the calculation functions in the control unit 26 are physically located in another apparatus (e.g. a PC).

Figure 2:
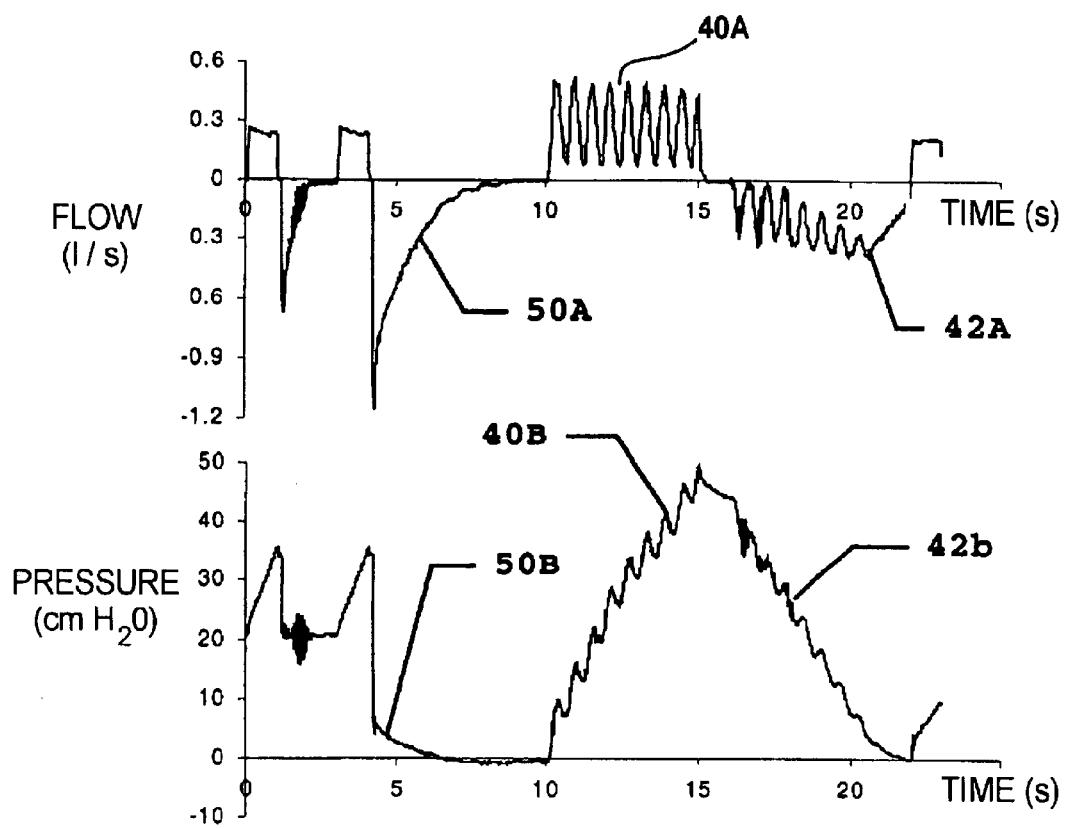
FIG. 2 is a diagram illustrating the modulation of flow during inspiration and expiration.
Figure 3:
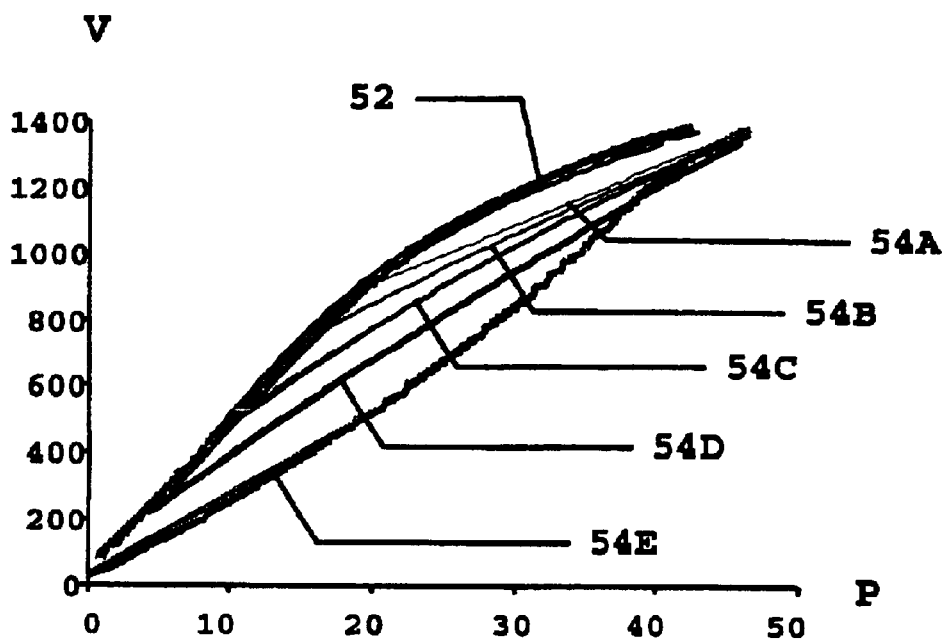
FIG. 3 is a diagram illustrating inspiratory and expiratory pressure-volume relationships.
Figure 4:
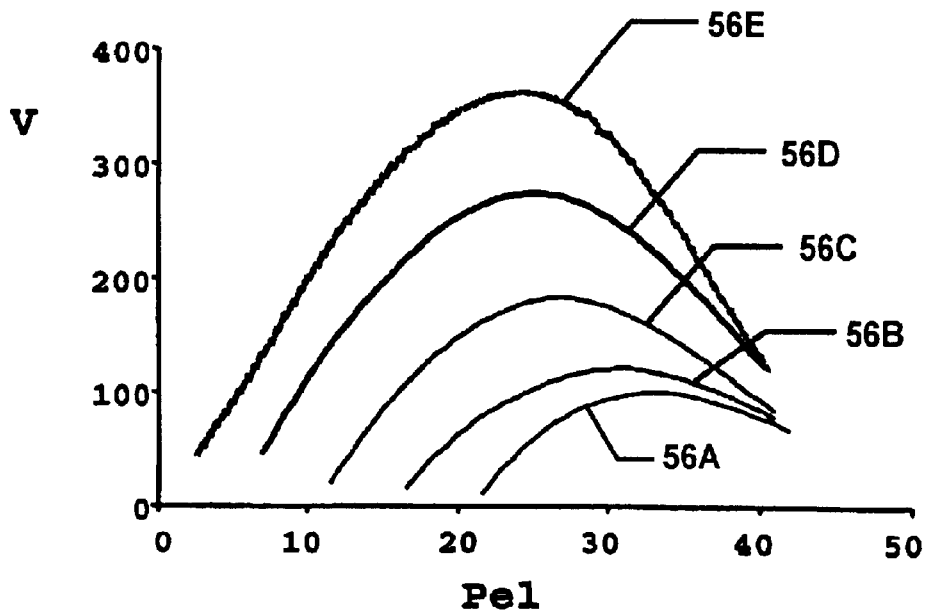
FIG. 4 illustrates one possible evaluation of hysteresis from the diagram in FIG. 3.

FIGS. 2, 3 and 4 are diagrams of curves recorded in experiments in which the method according to the invention was applied. The set-up is identical in certain respects with a set-up taught in detail in the aforementioned Swedish Patent No. 506521. The description below therefore simultaneously refers to all of FIGS. 2, 3 and 4.

An electrically controlled ventilator, such as the Servo Ventilator 900C (Siemens-Elema, Solna, Sweden), is used with an electronic units referred to as a Ventilator/Computer Interface (VCI) and a personal computer.

When the computer sends an analog signal through the VCI to one of the ventilator's control inputs, the computer assumes control of the function in question. It takes control of the value for the function set on the ventilator's control panel.

The computer has a transistor/transistor-logic output signal that passes the VCI and is sent to the ventilator's input for external control (Slave Start Insp). A signal sent through this line triggers the ventilator to start a new inspiration, regardless of which respiratory phase is in progress at the time the signal is sent.

The VCI includes a number of functions intended to prevent unintentional computer control of the ventilator. Thus, the VCI discovers the regular change between the ventilator's inspiratory and expiratory phases. If the changes do not occur at predetermined intervals, corresponding to a slowest breathing rate, a signal is emitted that terminates the signals, sent via the VCI, for computer control of the ventilator. Two relays connected in series are used to guarantee safety.

During measurement of mechanics, the apparatus, formed by the ventilator, VCI and computer, operates with the computer's software as follows. As soon as equipment is activated, the signals for flow and pressure are continuously displayed on the computer screen after analog-to-digital conversion at a frequency of 50 Hz. The patient's identity is specified in a first step in a computer/operator dialogue. The type of tube connector used between the patient and ventilator, including a tracheal tube and a humidifying filter, is specified for the purpose of facilitating correction of the resistive pressure drop across the system.

The planned study is then defined. The ventilator, according to known methods, can perform both volume-controlled and pressure-controlled ventilation. After the desired ventilator settings have been made, the computer therefore issues special queries as to whether ventilation is to be pressure-controlled or volume controlled, the duration of inspiration and the pause as a percentage of the breathing cycle.

A sequence is then defined that constitutes the measurement process (FIG. 2) consisting of one normal breath. FIG. 2 indicates the flow F in the upper graph with inspiration 40A, expiration 42A and pressure P in the lower graph along with the inspiration 40B and expiration 42B.

A dialog between the user and the computer in which the measurement process is defined precedes measurement of pressure-volume loops. Thus, the user selects the sequence during which pressure-volume loops are to be measured. After a dialogue, a given measurement process can be saved for use as a default in subsequent measurement of the same or other patients. A measurement process stored as a default can be modified in one or more respects before subsequent measurements. Definition of a measurement process includes the number of loops to be studied as well as start and stop values for the pressures each individual loop is to encompass. Stop values can alternatively be the volume the inspiratory limbs of a loop are to cover. This volume can be stated in ml or as the prevailing tidal volume Vt. The duration of the expiration preceding each loop also is determined. The form of modulation of inspiration and expiration respectively is also determined. In a preferred embodiment, inspiratory and expiratory flows are subjected to sinusoidal modulation. In another embodiment, modulation is in the form of triangle waves with a constant increase and decrease rate for flow in each wave.

Other waveforms may be preferable for technical reasons. In order to characterize flow modulation, wave cycle duration or wave depth are set. In the preferred embodiment flow can be set by the operator at values from zero flow to twice the mean flow during a normal inspiration. Pre-selected times for implementation of the measurement process, or only after an operator's manual command, also are specified in the dialog.

Following the dialog in which the measurement process is defined, the computer displays the process according to the following example and asks whether the answers are correct. If the operator replies 'no', the following corrections can be made:

EXAMPLE

No. of loops: =5
Starting values for pressure: =20, Step: −5 cmH20
No. of normal breaths between each loop: 6
Duration of preceding expiration: 6 s
End values for pressure, not selected, safety level: 50 cmH20
Volume range for loops: 1400 ml
Insufflation duration: 6 s
Exsufflation duration: 6 s
Sinusoidal modulation: 1.66 Hz Modulation depth: 100%
Time for measurement: At a manual command
Is the above correct, Yes/no? Yes Answers entered by the operator during the dialogue in the above example are in italics.

The measurement sequence starts at a pre-selected time or after a manual command. According to the above dialog, the sequence has five loops, the first of which starts at a pressure of 20 cmH20, with subsequent loops at successively lower pressures.

The measurement sequence starts when the computer sends analog signals to the respirator for control of the respirator's rate and end-expiratory pressure (PEEP). The signals controlling frequency and PEEP have the levels required for subsequent insufflation of gas to have the duration and starting value for pressure selected by the operator according to the above. Insufflation, subjected to sinusoidal modulation, then starts. During this operation, the computer sends an analog signal to the respirator for controlling the frequency in such a way that insufflation has the duration selected by the operator. The computer calculates the mean flow during insufflation in such a way that the volume range and the end value for pressure respectively are achieved during insufflation. The control of flow is according to principles that differ for volume-controlled and pressure-controlled-ventilation, respectively.

In volume-controlled ventilation (FIG. 2), the respirator primarily controls flow during inspiration. The computer emits an analog signal corresponding to the flow desired at every instant during insufflation. This flow is initially zero and increases sinusoidally up to a peak calculated by the computer from the range set for the volume of the loops, the duration of insufflation and the depth of modulation. The respirator ensures, through its built-in system for negative feedback, that flow during insufflation closely follows the intended sinusoidally modified flow.

In pressure-controlled ventilation, the respirator primarily controls pressure in the airways during insufflation. The computer calculates the way in which pressure is to be regulated in order to control the flow so that it closely tallies with the desired sinusoidal flow. By analyzing the preceding breath or a preceding sinusoidal insufflation, the computer calculates resistance in the patient's respiratory system during inspiration, RI, and a value for compliance. This can be done in a number of known ways. Insufflation begins while the computer sends an analog signal to the respirator regulating inspiratory pressure, PI. A low-voltage signal is first emitted. The flow measured by the inspiratory flow sensor is subjected to analogue/digital conversion in the computer and compared to the intended flow at every instant. The difference constitutes an error signal, Ffel. In the next step, the computer calculates the error in inspiratory pressure, Pfel, causing the error in flow, Ffel.

$$Pfel = -Ffel \cdot RI$$

The signal controlling inspiratory pressure is corrected by a value corresponding to Pfel. The calculated value for Pfel is traditionally entered into a digital system for PID-type negative feedback as programmed into the computer controlling ventilation. The signal fed into the ventilator in order to control inspiratory pressure is corrected by a value corresponding to the output signal from the inspiratory PID system. Since inspiratory pressure in the respirator is expected to rise over time in proportion to flow and in inverse proportion to compliance, the integrated component in the PID system is assigned a starting value proportional to flow divided by compliance. The degree of amplification in the PID system is selected so it produces optimal damping in order to prevent self-oscillation while simultaneously providing the fastest and most correct control of PI possible and, accordingly, of flow during insufflation. Insufflation with sinusoidal flow continues until one of the values for duration, volume range, selected end pressure or safety limit is reached.

Flow-modulated expiration follows flow-modulated insufflation.

The elastic rebound pressure, Pel, built up in the lungs and thorax during the preceding insufflation from the respirator provides the driving force during expiration and declines at every moment during expiration as a result of the ongoing decline in volume. The flow rate during flow-modulated expiration depends on resistance in the patient's respiratory system, in addition to Pel, and the pressure in the respirator's expiratory circuit, PE. Regulation of the latter pressure enables the computer/respirator to achieve the intended flow modulation during expiration according to the dialog between the operator and the computer. The resistance to flow in the patient's respiratory system is estimated during expiration, RE, by analysis of breaths preceding flow-modulated expiration or of previous flow-modulated expiration. The expiratory flow is read during the flow-modulated expiration using the computer's analog-digital converter. The measured value is compared to the reference value corresponding to the intended value for modulated flow at the same instant. The difference constitutes an error value for flow, Ffel. Ffel is used in calculating the magnitude of the error in pressure in the respirator's expiratory circuit in order to restore flow to the reference value, Pfel. The aforementioned estimated value for RE is used for this purpose. If expiratory flow is greater than the reference value, Ffel is positive because PE is too low. Pfel is then negative and should be increased by (-Rpat·Ffel).

$$Pfel = -RE \cdot Ffel$$

The calculated value for Pfel is entered in the conventional manner into a digital system for PID-type negative feedback that is programmed into the computer controlling ventilation. The signal entered into the computer in order to control PEEP is corrected by a value corresponding to the output signal from the PID system. The system's degree of amplification is selected so it produces optimal damping in order to prevent self-oscillation while simultaneously permitting the fastest and most correct control of PE possible and, accordingly, of expiratory flow.

After the first pressure-volume loop recorded, the respirator institutes the number of breaths selected between consecutive pressure-volume loops. The selected number of pressure-volume loops is then performed in the same way as above with the starting values selected for PEEP. FIG. 2 shows an example of flow and pressure signals recorded during the final loop after a dialog that followed the above example. As previously noted, the loop is preceded by a prolonged expiration 50A, 50B.

The data are automatically analyzed after all the loops have been recorded (FIG. 3). All the data for flow and pressure, from one or more recorded pressure-volume loop (s), are used in the calculation phase. According to the preferred embodiment, the parameters describing the respiratory system's resistive and elastic properties are estimated in a process based on an iterative numerical technique. According to an alternative embodiment, the calculation is performed according to other known analytical methods especially suitable for measurement in smaller pressure or volume ranges in which non-linearity can be described with formulas for analytical estimation of parameters.

According to the preferred embodiment, pressure in the trachea, Ptr, is calculated by subtracting the pressure drop across the system of tubing from pressure measured in the airways. The pressure gradient is calculated according to known principles utilising Rohrer's equation. This equation describes the pressure gradient in a system with turbulent flow. Ptr overcomes the respiratory system's resistive and elastic impedance. The flow in the patient's airways, Flv, is calculated by subtracting the flow corresponding to the compression of air in the tubing and tube stretching during inspiration and the reverse during expiration. The values for Ptr and Flv recorded during each insufflation with the subsequent expiration are analyzed in order to determine parameters governing resistance and equations describing the way in which Pel varies during each inspiration and expiration. They jointly describe the recorded pressure-volume loops. The results are graphically illustrated according to the FIG. Pel/V loops. FIG. 3 shows an example representing a case with adult respiratory distress syndrome (ARDS). Loops were recorded according to the aforementioned dialogue from 20, 15, 10, 5 to zero cm H20. The expiratory pressure-volume relationships 52 for the different loops coincide almost exactly, making it impossible to separate them in FIG. 3. The inspiratory pressure-volume relationships differ increasingly from each other, so the loops become increasingly wider as PEEP declines. A first pressure-volume relationship 54A can be distinguished in the figure for 20 cm H2O for PEEP, a second pressure-volume relationship 54B for 15 cm H2O for PEEP, a third pressure-volume relationship 54C for 10 cm H2O for PEEP, a fourth pressure-volume relationship 54D for 5 cm H2O for PEEP and a fifth pressure-volume relationship 54E for 0 cm H2O for PEEP. The increase in the width of the loops, i.e. the increasing hysteresis, constitutes the most important information obtained according to the invention. In a preferred embodiment, the information is further processed by measurement of the width of the volume phase of each loop throughout its entire range along the X-axis, this axis representing elastic pressure. The result is graphically illustrated in the example in FIG. 4. FIG. 4 clearly shows a first width curve 56A corresponding to the width at 20 cm H2O for PEEP, a second width curve 56B corresponding to the width of 15 cm H2O for PEEP, a third width curve 56C corresponding to the width at 10 cm H2O for PEEP, a fourth width curve 56D corresponding to 5 cm H2O for PEEP and a fifth width curve 56E corresponding to the width at 0 cm H2O for PEEP.

The operator interprets the results as shown in the example. Increasing hysteresis when the loop representing a breath begins at a low value for PEEP reflects increasing collapse and re-expansion of the lung during each breath. This leads to lung damage. There is always some hysteresis for other reasons, such as the viscoelastic properties of the respiratory organs. If the operator finds that hysteresis of 100 ml is acceptable but not 150 ml, she/he can select a value for PEEP of 15 cm H2O according to the example.

The above remarks about sinusoidal modulation of insufflations and expirations also apply if some other form of flow modulation is selected according to alternative embodiments. If the depth of modulation is shallow or zero, this means that resistance cannot be accurately determined, or perhaps not at all, during the insufflation and expiration respectively covered by the loop. According to alternative embodiments, resistance can instead be measured with other methods that, however, are regarded as less precise. Keeping flow during inspiration and expiration on a low level can compensate for the reduced precision in resistance measurement.

According to the preferred embodiment, studying loops starting at a pressure lower than the lowest value that can reasonably be used for PEEP, in order to avoid VILI in the individual patient, is not necessary or desirable, nor is the study of loops from a number of breaths always necessary. According to an alternative embodiment, the computer is programmed so measurement sequences of one or two loops are automatically run with starting values for pressure and intervals set by the operator. The results of hysteresis measurements on every occasion are compared to the desirable or acceptable limits set by the operator. An alarm is sounded if hysteresis is excessive. The level for PEEP or tidal volume can also be adjusted automatically with limit values set by the operator.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for examining pulmonary mechanics of a respiratory system, comprising the steps of:
    modulating a flow of gas exiting a respiratory system during an expiration;
    determining an expiratory volume of said gas exiting said respiratory system during said expiration;
    determining an expiratory variation in pressure in said respiratory system during said expiration; and
    determining an expiratory pressure-volume relationship from said expiratory volume and said expiratory variation in pressure.

2. A method as claimed in claim 1 comprising the additional steps of:
    modulating a flow of gas entering into said respiratory system during an inspiration;
    determining an inspiratory volume of said gas entering into said respiratory system during said inspiration;
    determining an inspiratory variation in pressure in said respiratory system during said inspiration; and
    determining an inspiratory pressure-volume relationship from said inspiratory volume and said insoiratory variation in pressure.

3. A method as claimed in claim 2 comprising prolonging a duration of said expiration immediately preceding said inspiration.

4. A method as claimed in claim 2 comprising the additional steps of:
    comparing said inspiratory pressure-volume relationship with said expiratory pressure-volume relationship; and
    determining a hysteresis between said inspiratory pressure-volume relationship and said expiratory pressure-relationship.

5. A method as claimed in claim 4 comprising determining said hysteresis by determining a difference in volume, for given values of pressure, between said inspiratory pressure-volume relationship and said expiratory pressure-volume relationship.

6. A method as claimed claim 4 comprising determining said hysteresis by determining a pressure gradient, for given values of volume, between said inspiratory pressure-volume relationship and said expiratory pressure-volume relationship.

7. A method as claimed in claim 4 comprising determining said hysteresis for a plurality of inspiratory pressure-volume relationships respectively compared with a plurality of expiratory pressure-volume relationships obtained over a plurality of respiratory cycles, each of said respiratory cycles having a different value of a selected parameter, and said selected parameter being selected, for each of said plurality of respiratory cycles, from the group consisting of positive end-expiratory pressure, peak inspiratory pressure, and tidal volume.

8. A breathing apparatus comprising:
    a pneumatic unit adapted for communication with a respiratory system of a patient for regulating a flow and a pressure of gases into and out of respiratory system;
    a sensor system for measuring said pressure and said flow and for generating a sensor system output dependent thereon;
    a control unit connected to said pneumatic unit and to said sensor system, and
    said control unit operating said pneumatic unit to modulate a flow of gas exiting a respiratory system during an expiration and, from said sensor system output, determining a volume of said gas exiting said respiratory system during said expiration, determining a variation in pressure in said respiratory system during said expiration, and determining an expiratory pressure-volume relationship from said expiratory volume and said expiratory variation in pressure.

9. A breathing apparatus as claimed in claim 8 wherein said control unit additionally:
    operates said pneumatic unit to modulate a flow of gas entering into said respiratory system during an inspiration, and, from said sensor system output, determining a volume of said gas entering into said respiratory system during said inspiration, determining a variation in pressure in said respiratory system during said inspiration, and determining an inspiratory pressure-volume relationship from said inspiratory volume and said inspiratory variation in pressure.

10. A breathing apparatus as claimed in claim 9 wherein said control unit operates said pneumatic unit to prolong a duration of said expiration immediately preceding said inspiration.

11. A breathing apparatus as claimed in claim 9 wherein said control unit additionally compares said inspiratory pressure-volume relationship with said expiratory pressure-volume relationships, and determines a hysteresis between said inspiratory pressure-volume relationship and said expiratory pressure-relationship.

12. A breathing apparatus as claimed in claim 11 wherein said control unit determines said hysteresis by determining a difference in volume, for given values of pressure, between said inspiratory pressure-volume relationship and said expiratory pressure-volume relationship.

13. A breathing apparatus as claimed claim 11 wherein said control unit determines said hysteresis by determining a pressure gradient, for given values of volume, between said inspiratory pressure-volume relationship and said expiratory pressure-volume relationship.

14. A breathing apparatus as claimed in claim 11 wherein said control unit determines said hysteresis for a plurality of inspiratory pressure-volume relationships respectively compared with a plurality of expiratory pressure-volume relationships obtained over a plurality of respiratory cycles, each of said respiratory cycles having a different value of a selected parameter, and said selected parameter being selected, for each of said plurality of respiratory cycles, from the group consisting of positive end-expiratory pressure, peak inspiratory pressure, and title volume.

15. A breathing apparatus as claimed in claim 14 wherein said control unit automatically adapts said selected parameter dependent on said hysteresis.

16. A breathing apparatus as claimed in claim 8 further comprising an interface connected to said control unit for displaying a representation of at least said expiratory pressure-volume relationship.

17. A breathing apparatus as claimed in claim 16 wherein said user interface allows entry of parameters into said control unit.

* * * * *